United States Patent [19]

Takeichi et al.

[11] Patent Number: 5,695,683
[45] Date of Patent: Dec. 9, 1997

[54] FERROELECTRIC LIQUID CRYSTAL MIXTURE

[75] Inventors: Ayako Takeichi, Tokorozawa, Japan; Gerhard Illian, Erftstadt, Germany

[73] Assignee: Hoechst Aktiengesellschaft, Frankfurt, Germany

[21] Appl. No.: 315,091

[22] Filed: Sep. 29, 1994

[30] Foreign Application Priority Data

Sep. 30, 1993 [JP] Japan .................. 5-245485

[51] Int. Cl.$^6$ .................. C09K 19/34; C09K 19/12; C09K 19/32
[52] U.S. Cl. .................. 252/299.61; 252/299.62; 252/299.66
[58] Field of Search .................. 252/299.62, 299.66, 252/299.61

[56] References Cited

U.S. PATENT DOCUMENTS

| | | | |
|---|---|---|---|
| 4,585,575 | 4/1986 | Sugimori et al. | 252/299.61 |
| 4,695,651 | 9/1987 | Higuchi et al. | 560/141 |
| 4,732,699 | 3/1988 | Higuchi et al. | 252/299.66 |
| 4,808,333 | 2/1989 | Huynh-Ba et al. | 252/299.66 |
| 4,831,182 | 5/1989 | Higuchi et al. | 560/59 |
| 4,876,026 | 10/1989 | Saito et al. | 252/299.61 |
| 4,891,151 | 1/1990 | Wingen et al. | 252/299.61 |
| 4,906,401 | 3/1990 | Düball et al. | 252/299.61 |
| 4,952,699 | 8/1990 | Yong et al. | 548/136 |
| 4,952,858 | 8/1990 | Higuchi et al. | 252/299.66 |
| 5,047,170 | 9/1991 | Huynh-Ba et al. | 252/299.6 |
| 5,071,589 | 12/1991 | Düball et al. | 252/299.61 |
| 5,076,961 | 12/1991 | Nakamura et al. | 250/299.61 |
| 5,167,856 | 12/1992 | Harada et al. | 252/299.01 |
| 5,169,556 | 12/1992 | Mochizuki et al. | 252/299.62 |
| 5,182,047 | 1/1993 | Coates et al. | 252/299.66 |
| 5,183,586 | 2/1993 | Terada et al. | 252/299.61 |
| 5,200,109 | 4/1993 | Iwaki et al. | 252/299.61 |
| 5,217,645 | 6/1993 | Iwaki et al. | 252/299.61 |
| 5,252,253 | 10/1993 | Gray et al. | 252/299.62 |
| 5,286,409 | 2/1994 | Düball et al. | 252/299.61 |
| 5,348,684 | 9/1994 | Gemmerling et al. | 252/299.61 |
| 5,397,504 | 3/1995 | Tsuchiya et al. | 252/299.66 |

FOREIGN PATENT DOCUMENTS

| | | |
|---|---|---|
| 0284008 | 9/1988 | European Pat. Off. |
| 0288813 | 11/1988 | European Pat. Off. |
| 0307880 | 3/1989 | European Pat. Off. |
| 0318423 | 5/1989 | European Pat. Off. |
| 0451821 | 10/1991 | European Pat. Off. |
| 0308794 | 3/1994 | European Pat. Off. |
| WO 90/11336 | 10/1990 | WIPO |
| WO 90/11547 | 10/1990 | WIPO |
| WO 91/08272 | 6/1991 | WIPO |

OTHER PUBLICATIONS

Atsuo Fukuta et al., Structure and Physical Properties of Ferroelectric Liquid Crystals, Corona pp. 283–284 (1992).

*Primary Examiner*—C. H. Kelly
*Attorney, Agent, or Firm*—Curtis, Morris & P C

[57] ABSTRACT

A ferroelectric liquid crystal mixture which does not lower the conventional transition temperature to the ferroelectric phase (60° C. or above), which maintains the Sa phase within a suitable temperature range, and which is useful for reducing the cone angle is disclosed. The ferroelectric liquid crystal mixture contains at least one of the compounds represented by the following general formula 1 to 3, and exhibits a Sa/Sc phase transition temperature of 60° C. or more and a cone angle of 47 degree or less at some temperature between 15° C. and 35° C.:

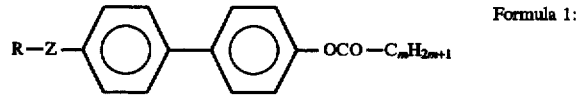

Formula 1:

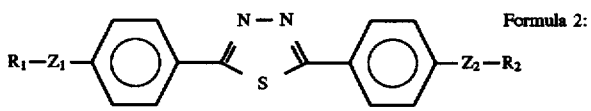

Formula 2:

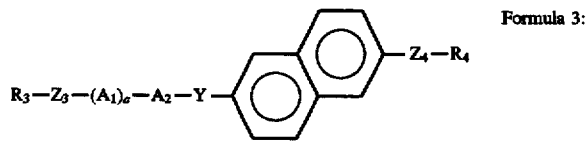

Formula 3:

7 Claims, No Drawings

FERROELECTRIC LIQUID CRYSTAL MIXTURE

FIELD OF THE INVENTION

This invention relates to a ferroelectric liquid crystal mixture used for a ferroelectric liquid crystal display device.

In particular in the last decade, liquid crystals have been introduced into various technical areas where electro-optical and display device properties are required (for example in watch, calculator and typewriter displays). These display devices are based on the dielectric alignment effects in the nematic, cholesteric and/or smectic phases of the liquid-crystalline compounds, where, caused by the dielectric anisotropy, the molecular long axes of the compounds adopt a preferred alignment in an applied electric field. The conventional response times in these display devices are too long for many other potential areas of application of liquid crystals. This disadvantage is particularly noticeable if a large number of pixels have to be addressed. The production costs of equipment containing relatively large screen areas are then generally too high.

In addition to nematic and cholesteric liquid crystals, optically active smectic liquid-crystals phases have also been increasing in importance for a few years.

Clark and Lagerwall have been able to show that the use of ferroelekctric liquid-crystal systems in very thin cells give electro-optical switch or display elements which have response times faster by a factor of up to 1000 compared with conventional TN ("twisted nematic") cells (cf., for example, Lagerwall et al., "Ferroelectric Liquid Crystals for Displays", SID Symposium, October Meeting 1985, San Diego, Calif., USA). Due to these and other favorable properties, for example the possibility for bistable switching and the contrast which is virtually independent of the viewing angle, FLCs are fundamentally very suitable for the abovementioned areas of application, for example via matrix adressing. Due to their high contrast and speed, ferroelectric liquid crystals are also particularly suitable in the area of spatial light modulators (cf., for example, U. Efron in "Spatial Light Molulators and Applications", SPIE, Vol. 1150, p. 46 ff).

As described above, a high speed and a high contrast can be achieved with FLC devices as compared with conventional TN type liquid crystal display devices. In the FLC device, values of the speed and the contrast vary reciprocally as described below. More specifically, the contrast is the ratio between the transmission in the bright state and the transmission in the dark state, and the transmission in the bright state depends on the angle between two extinction positions $2\theta_{\mathit{eff}}$ ($\theta_{\mathit{eff}}$ is the effective tilt angle) in accordance with the following equation:

$$\text{Transmission} = \sin^2(4\theta_{\mathit{eff}}) \times \sin^2(\pi d \Delta n/\lambda)$$

wherein:
  d: cell thickness
  Δn: refraction anisotropy
  λ: wavelength of incident light The switching speed, on the other hand, is determined in accordance with the following equation:

$$\text{Switching Time} = a \times \sin(\theta_{\mathit{eff}}) \ (a\text{:constant})$$

Some relative values of the switching speed and the contrast calculated by the above equations are shown in Table 1 below:

TABLE 1

Light Transmission in Bright State and Pulse Width (a relative value to the value at $2\theta_{\mathit{eff}} = 45$ degree)

| $2\theta_{\mathit{eff}}$ | 55 | 50 | 45 | 40 | 35 | 33 | 30 | 25 | 20 |
|---|---|---|---|---|---|---|---|---|---|
| Transmission | 88 | 97 | 100 | 97 | 88 | 83 | 75 | 59 | 41 |
| Pulse Width (Switching Time) | 120 | 110 | 100 | 89 | 79 | 74 | 68 | 56 | 45 |

According to Table 1, the contrast reaches its maximum value when the angle between the two extinction positions $2\theta_{\mathit{eff}}$ is 45 degree, and the speed increases as $2\theta_{\mathit{eff}}$ approaches 0 degree. As set forth above, in the range of $2\theta_{\mathit{eff}} < 45$ degree, achievement of both a high transmission and a high speed is apparently contradictory. For this reason, when the liquid crystal cell is used as a display device, these properties must be optimized.

For example, a liquid crystal mixture having $2\theta_{\mathit{eff}}$ of 33 degree has a transmission of only 80%, as compared with that of 45 degree, the switching speed, however, is improved by 26%.

In recent years, a study has been made with respect increasing both the effective angle $2\theta_{\mathit{eff}}$ and the cone angle which is twice the angle between a phase normal of the smectic phase and the director of the molecule (i.e., an average direction of long axis of the molecule). This can be achieved by the electric field treatment of the chevron oriented cell or by using an alignment layer inducing a high pretilt angle. In order to achieve the speed and the contrast suitable for the display device in the above-described modes, a liquid crystal mixture having a $2\theta_{\mathit{eff}}$ of from 28 to 45 degree is required. Alternatively, since the effective angle is generally smaller than the cone angle by about 2 degree, the cone angle is required to be 30 to 47 degree.

Conventional liquid crystal mixtures mainly contain compounds such as phenylpyrimidines, phenyl benzoates, phenylpyridines, pyridylpyrimidines, difluorophenylpyrimidines, phenylfluoropyridines and diphenylpyrimidines. These compounds are disclosed in examples of the prior art, for example, European Patent Publication Nos. 0284008, 0308794, 0307880, 0318423, 0288813 and 0451821, and International Publication Nos. 90/11547, 90/11336 and 91/08272. In these liquid crystal mixtures, $2\theta_{\mathit{eff}}$ is about 45 degree and about 55 degree at Sc/Sa phase transition temperatures of 60° C. and 70° C., respectively.

In order to achieve the above-described suitable switching speed and contrast, it is necessary to reduce the cone angle of the liquid crystal mixture. The cone angle is generally easily reduced by lowering the phase transition temperature. However, since an operable temperature range of the liquid crystal material becomes narrow as the phase transition temperature lowers, an application of the liquid crystal material having a low phase transition temperature to a display device is not practical. For applying it to the display device, it is required that the liquid crystal material generally has a ferroelectric phase at a temperature of 60° C. or above in order to ensure the operable temperature range of the liquid crystal material. Also, the cone angle is reduced by adding a large amount of compounds having a broad Sa phase to the liquid crystal mixture (Atsuo Fukuta et al., "Structure and Physical Properties of Ferroelectric Liquid Crystal", Corona Co.).

However, this method has a disadvantage in that, since a transition point to the isotropic phase exceeds 100° C., the cell must be filled with the liquid crystal at a high temperature, and thus materials which constitute the cell are restricted.

DETAILED DESCRIPTION OF THE INVENTION

The ferroelectric liquid crystal mixture according to the present invention comprises at least one of the compounds represented by the following general formulae 1, 2 and 3, and having a Sc/Sa phase transition temperature of 60° C. or above and a cone angle of 47 degree or less at some temperature between 15° C. and 35° C.:

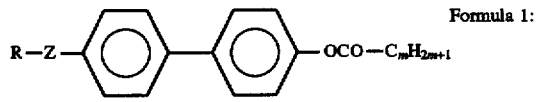

Formula 1:

wherein one or more hydrogen atoms of the aromatic ring may be substituted with a substituent selected from the group consisting of F, Cl and CN;

m is an integer of from 1 to 16;

R represents (a) a straight chain or branched chain alkyl group having from 2 to 16 carbon atoms, in which one or two non-adjacent —$CH_2$— groups may be substituted with —O—, —S—, —CO—, —CO—O—, —O—CO—, —CO—S—, —S—CO—, —CH=CH—, —C≡C—, —Si($CH_3$)$_2$—, a chiral epoxy group or —O—CO—O—; one or more hydrogen atoms of the alkyl group may be substituted with a substituent selected from the group consisting of F, Cl and CN; and a terminal methyl group may be substituted with a cyclopropyl group or a cyclohexyl group; or (b):

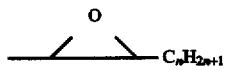

wherein n is an integer of from 1 to 10; and
Z is a single bond, —O—, —CO—O—, —O—CO—, —O—$CH_2$ or —$CH_2$O—; provided that, when R is (b), Z is —CO—O— or —$CH_2$—O—;

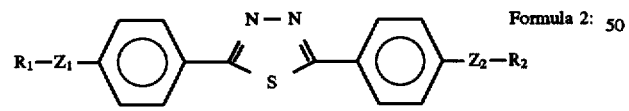

Formula 2:

wherein at least one optional =C—H group of the aromatic ring may be substituted with =C—F or =N—;

$R_1$ and $R_2$ each independently represents (a) a hydrogen atom;

(b) a straight chain or branched chain alkyl group having from 2 to 16 carbon atoms, in which one or two non-adjacent —$CH_2$— groups may be substituted with —O—, —S—, —CO—, —CO—O—, —O—CO—, —CO—S—, —S—CO—, —CH=CH—, —C≡C—, —Si($CH_3$)$_2$—, a chiral epoxy group or —O—CO—O—; one or more hydrogen atoms of the alkyl group may be substituted with a substituent selected from the group consisting of F, Cl and CN; and a terminal methyl group may be substituted with a cyclopropyl group or a cyclohexyl group; or (c):

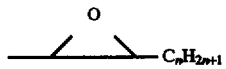

wherein n is an integer of from 1 to 10; and
$Z_1$ and $Z_2$ each represents a single bond, —O—, —CO—O—, —O—CO—, —O—$CH_2$— or —$CH_2$O—; provided that, when $R_1$ is (c), $Z_1$ is —CO—O— or —$CH_2$—O— and that, when $R_2$ is (c), $Z_2$ is —O—CO— or —O—$CH_2$—;

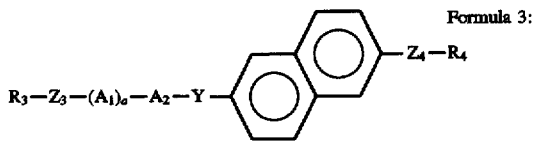

Formula 3:

wherein $A_1$ and $A_2$, which may be the same or different, each represents 1,4-phenylene in which one or two hydrogen atoms may be substituted with a substituent selected from the group consisting of F, Cl and CN, or pyrazine-2,5-diyl, pyridazine-3,6-diyl, pyridine-2,5-diyl or pyrimidine-2,5-diyl in which one or two hydrogen atoms may be substituted with F;

a is 0 or 1;

$R_3$ and $R_4$ each independently represents (a) a hydrogen atom;

(b) a straight chain or branched chain alkyl group having from 2 to 16 carbon atoms, in which one or two non-adjacent —$CH_2$— groups may be substituted with —O—, —S—, —CO—, —CO—O—, —O—CO—, —CO—S—, —S—CO—, —CH=CH—, —C≡C—, —Si($CH_3$)$_2$—, a chiral epoxy group or —O—CO—O—; one or more hydrogen atoms of the alkyl group may be substituted with a substituent selected from the group consisting of F, Cl and CN; and a terminal methyl group may be substituted with a cyclopropyl group or a cyclohexyl group; or (c):

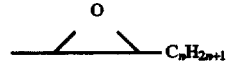

wherein n is an integer of from 1 to 10; Y is a single bond,
—O—CO—, —CO—O—, —O—$CH_2$— or —$CH_2$—O—; or Y is a single bond or —O—CO—; and
$Z_3$ and $Z_4$ each represents a single bond, —O—, —CO—O—, —O—CO—, —$CH_2$—O— or —O—$CH_2$—; provided that, when $R_3$ is (c), $Z_3$ is —CO—O— or —$CH_2$—O and that, when $R_4$ is (c), $Z_4$ is —O—CO— or —O—$CH_2$.

Preferably, the ferroelectric liquid crystal mixture according to the present invention comprises at least one of the liquid crystal compounds represented by the following general formulae 1, 2 and 3:

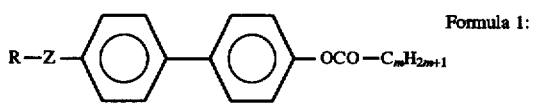

Formula 1:

wherein m is an integer of from 1 to 16;

R represents a straight chain or branched chain alkyl group having from 2 to 16 carbon atoms, in which one or two non-adjacent —CH$_2$— groups may be substituted with —O—, —CO—, —CO—O—, —O—CO— or —O—CO—O—, and a terminal methyl group may be substituted with a cyclopropyl group or a cyclohexyl group; and Z is a single bond, —O—, —CO—O—, —O—CO—, —CH$_2$—O— or —O—CH$_2$—;

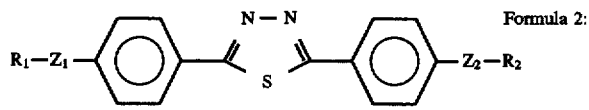

Formula 2:

wherein at least one optional =C—H group of the aromatic ring may be substituted with =C—F or =N—;

R$_1$ and R$_2$ each independently represents (a) a hydrogen atom;

(b) a straight chain or branched chain alkyl group having from 2 to 16 carbon atoms, in which one or two non-adjacent —CH$_2$— groups may be substituted with —O—, —CO—O—, —O—CO—, —Si(CH$_3$)$_2$—, a chiral epoxy group or —O—CO—O—, and a terminal methyl group may be substituted with a cyclopropyl group or a cyclohexyl group; or (c):

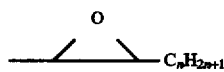

wherein n is an integer of from 1 to 10; and

Z$_1$ and Z$_2$ each represents a single bond, —O—, —CO—O—, —O—CO—, —O—CH$_2$— or —CH$_2$—O—; provided that, when R$_1$ is (c), Z$_1$ is —CO—O— or —CH$_2$—O— and that, when R$_2$ is (c), Z$_2$ is —O—CO— or —O—CH$_2$—;

Formula 3:

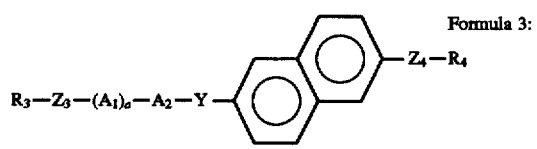

wherein A$_1$ and A$_2$, which may be the same or different, each represents 1,4-phenylene, pyridine-2,5-diyl or pyrimidine-2,5-diyl in which one or two hydrogen atoms may be substituted with F;

a is 0 or 1;

R$_3$ and R$_4$ each independently represents (a) a hydrogen atom;

(b) a straight chain or branched chain alkyl group having from 2 to 16 carbon atoms, in which one or two non-adjacent —CH$_2$— groups may be substituted with —O—, —CO—, —CO—O—, —O—CO—, —Si(CH$_3$)$_2$—, a chiral epoxy group or —O—CO—O—; and a terminal methyl group may be substituted with a cyclopropyl group or a cyclohexyl group; or (c):

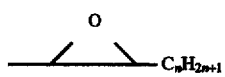

wherein n is an integer of from 1 to 10; Y is a single bond, —O—CO—, —CO—O—, —O—CH$_2$— or —CH$_2$—O— or Y is a single bond or —O—CO— and Z$_3$ and Z$_4$ each represents a single bond, —O—, —CO—O—, —O—CO—, —O—CH$_2$— or —CH$_2$—O; provided that, when R$_3$ is (c), Z$_3$ is —CO—O— or —CH$_2$—O— and that, when R$_4$ is (c), Z$_4$ is —O—CO— or —O—CH$_2$—.

Ferroelectric liquid crystal mixtures according to the invention have a S$_c$-S$_A$ phase transition temperature of 60° C. or more and a cone angle of 47° or less at some temperature between 15° C. and 35° C. preferably between 20° C. and 30° C. more preferably between 20° C. and 25° C.

When any of the compounds represented by the general formulae 1 to 3 above is contained in the liquid crystal mixture in an amount of preferably 5% or more, and more preferably from 10 to 50%, the transition temperature to the ferroelectric phase can be maintained at 60° C. or more, the Sa phase can be maintained in the appropriate temperature range, and the cone angle can be reduced.

Of the compounds represented by the general formula 1, preferred compounds include the compounds represented by the following general formula (1a):

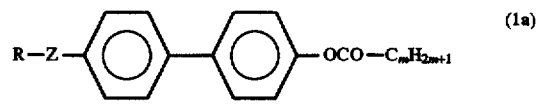

(1a)

wherein m is an integer of from 1 to 16; R represents a straight chain or branched chain alkyl group having from 2 to 16 carbon atoms, in which one or two non-adjacent —CH$_2$— groups may be substituted with —O—, —CO—, —CO—O—, —O—CO—, or —O—CO—O—, and a terminal methyl group may be substituted with a cyclopropyl group or a cyclohexyl group; and Z is a single bond, —O—, —CO—O— or —O—CO—. More preferably, Z in the formula (1a) represents —O— or —CO—O—.

Further, in the compounds represented by the general formula 1, R is preferably an n-alkyl group having from 1 to 16 carbon atoms.

Particularly preferred compounds represented by the general formula 1 include the following compounds.

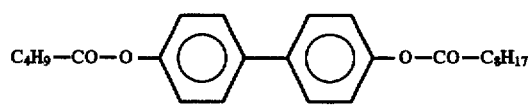

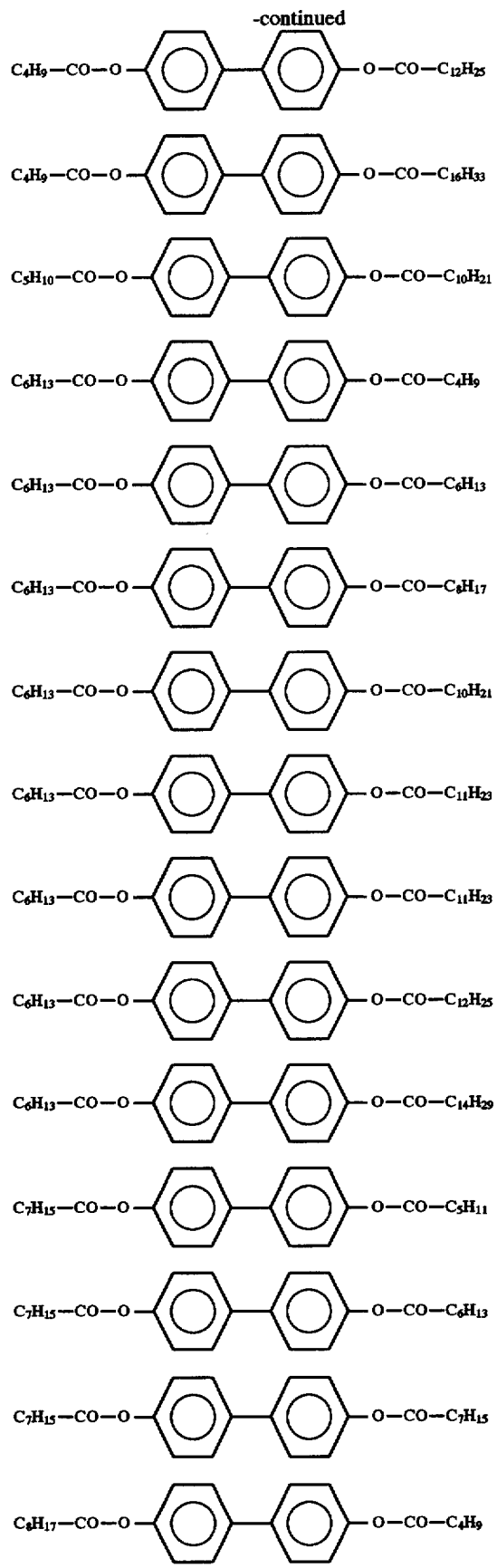

-continued
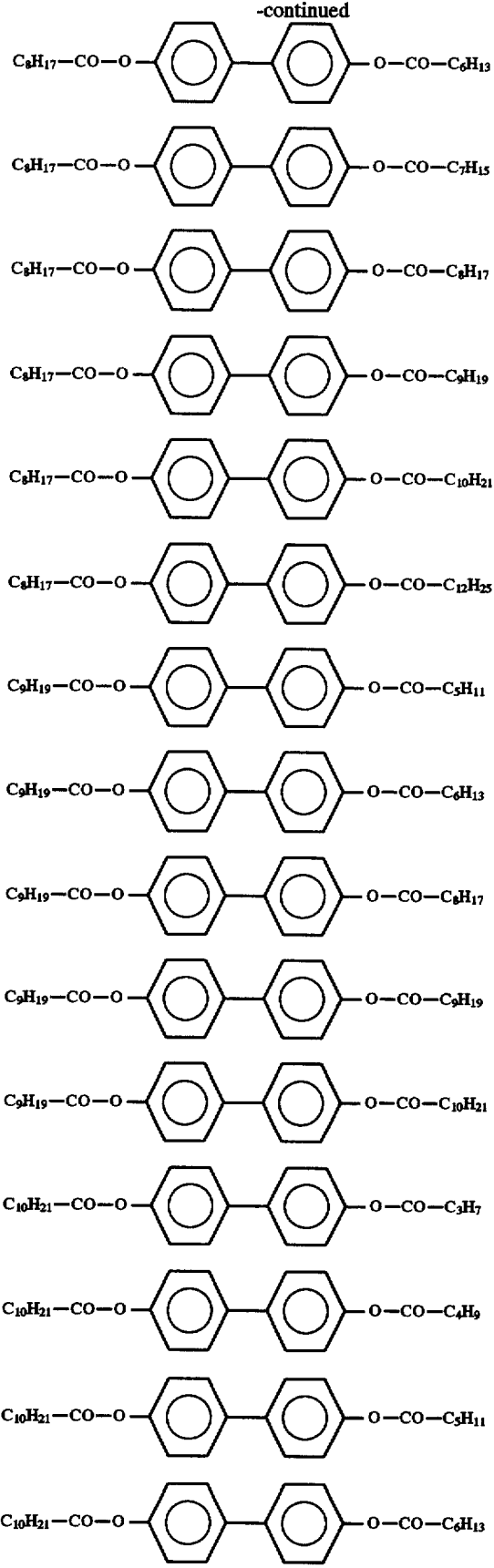

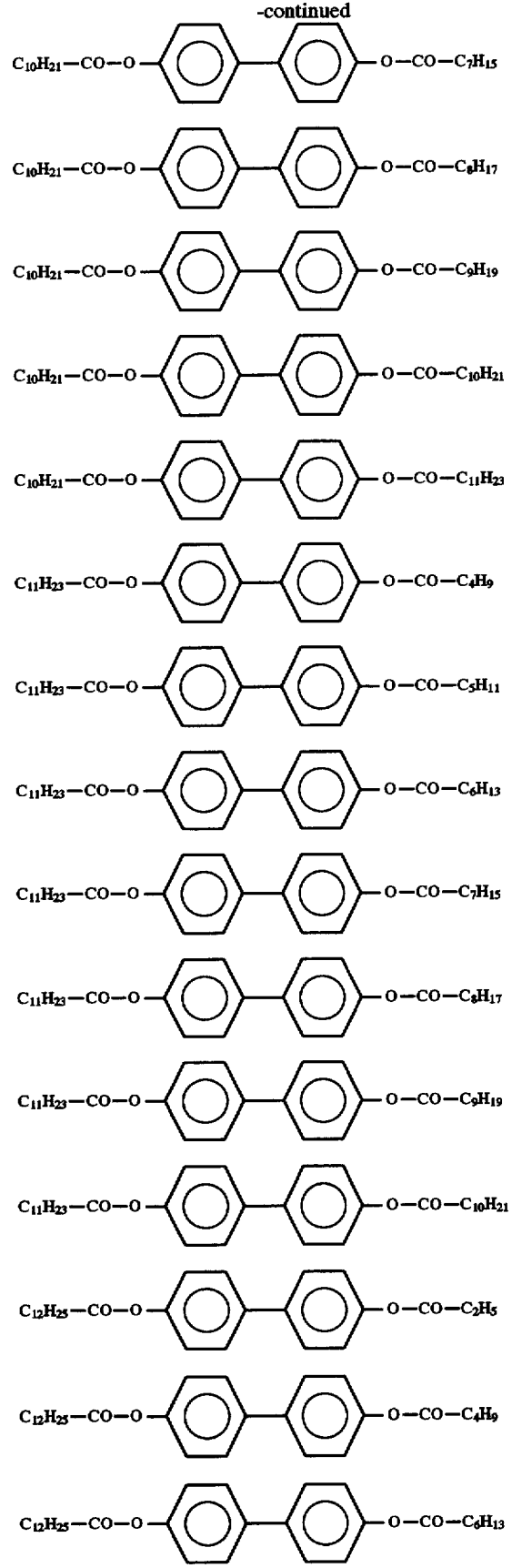

-continued
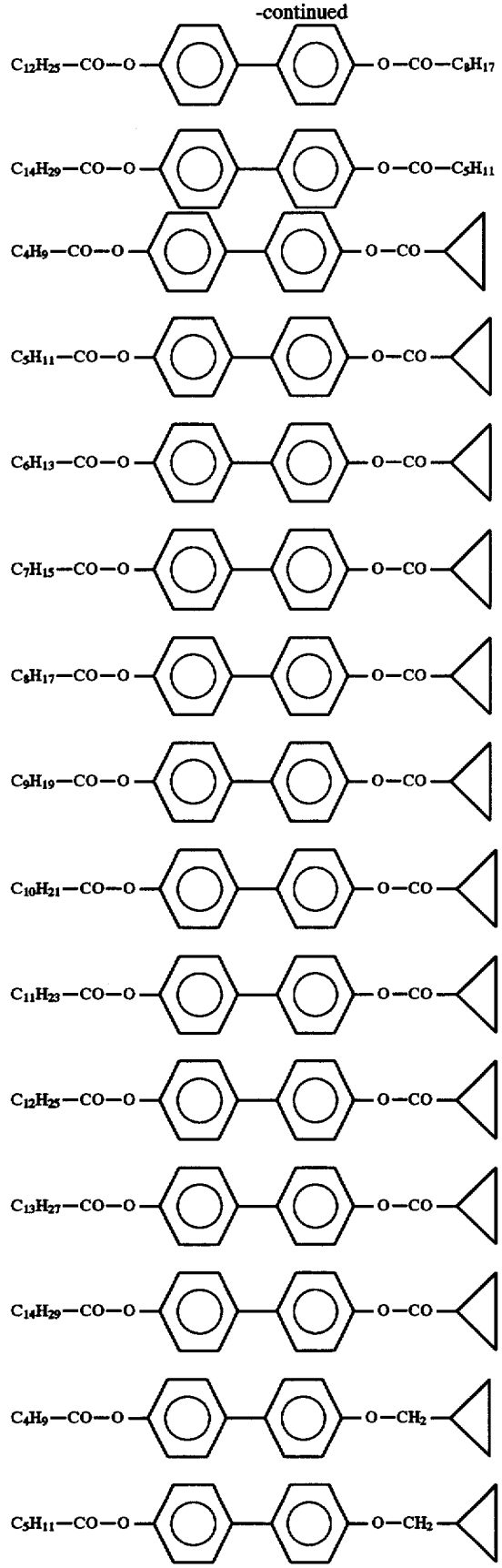

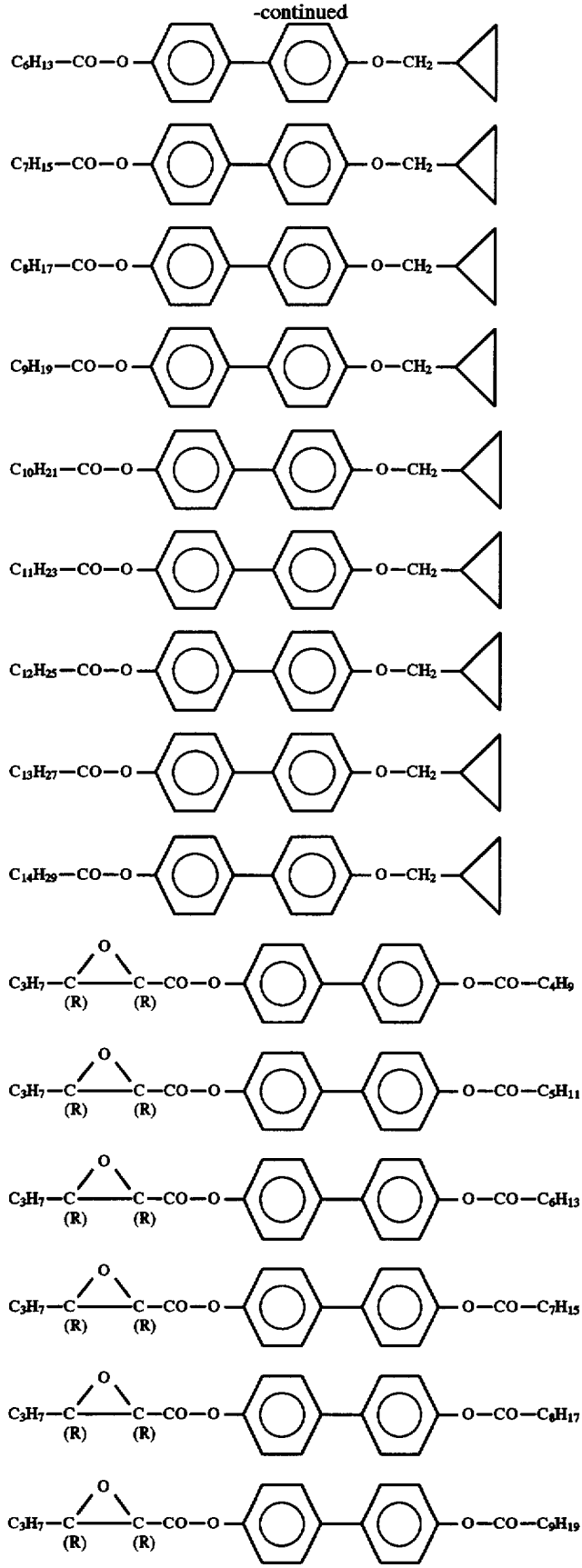

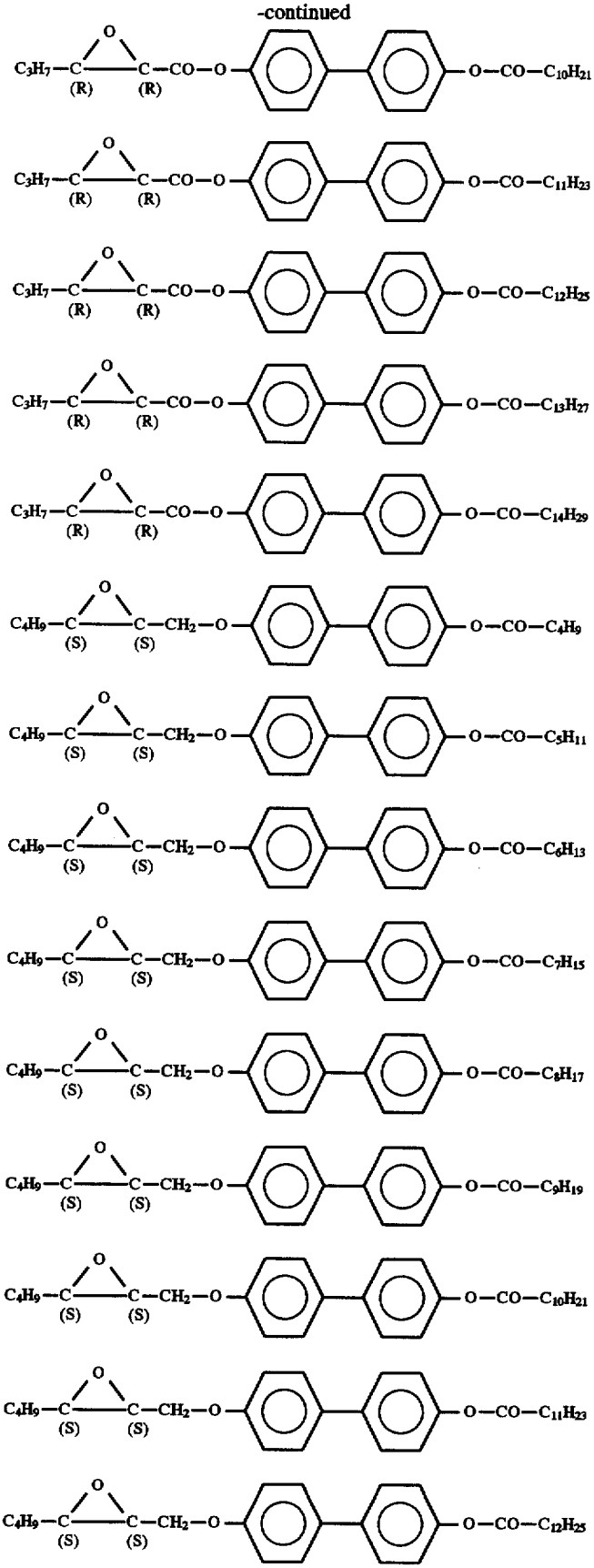

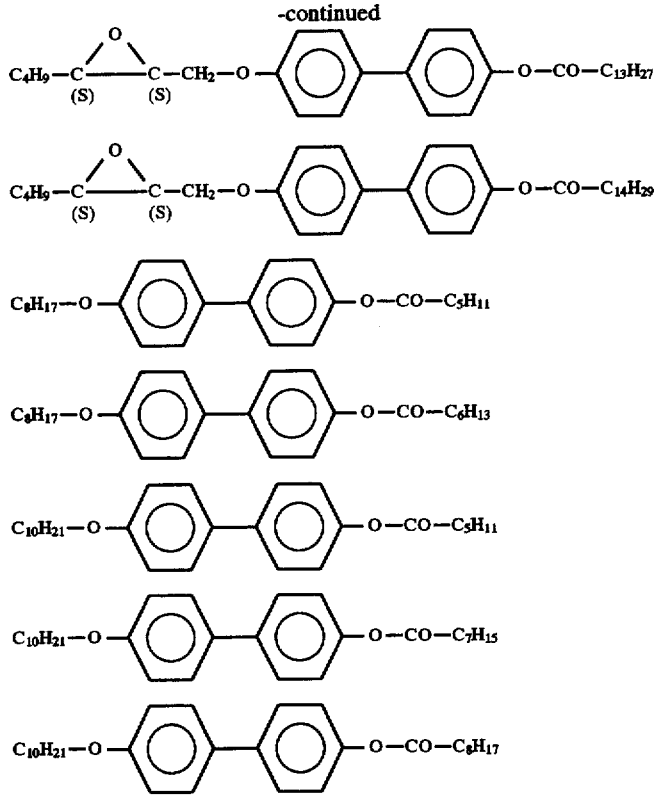

Of the compounds represented by the general formula 2, preferred compounds include the compounds represented by the following general formulae (2a), (2b), (2c) and (2d):

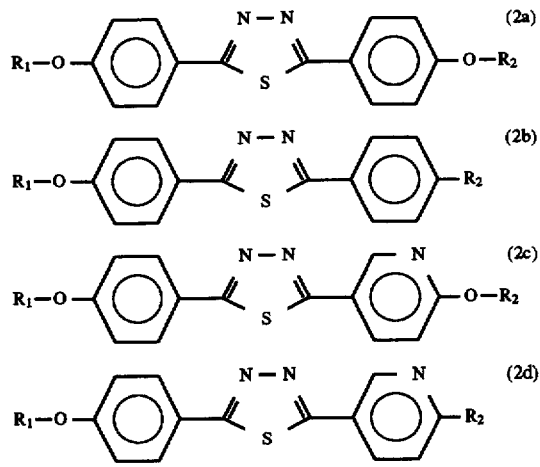

wherein $R_1$ is preferably an n-alkyl group having from 1 to 16 carbon atoms, and $R_2$ is preferably selected from the groups represented by the following formulae (2-i) to (2-v):

(2-i) an n-alkyl group having from 1 to 16 carbon atoms;

(2-ii)

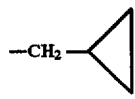

(2-iii)

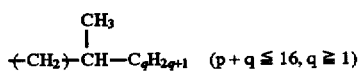

(2-iv) a cyclohexyl group; and (2-v) H.

Further, in the compounds represented by the formulae (2a), (2b) and (2c), $R_1$ and $R_2$ are preferably an n-alkyl group having from 1 to 16 carbon atoms.

Particularly preferred compounds represented by the general formula 2 include the following compounds.

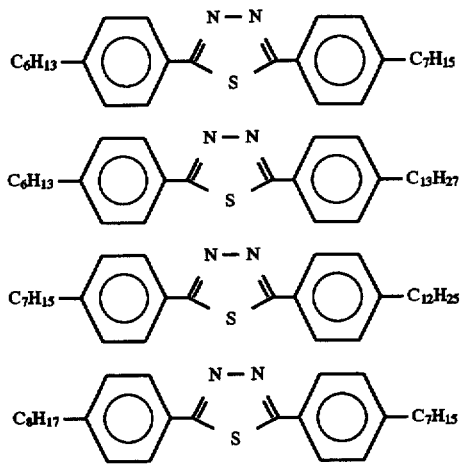

-continued (structures continued - thiadiazole compounds with various alkyl and alkoxy substituents)

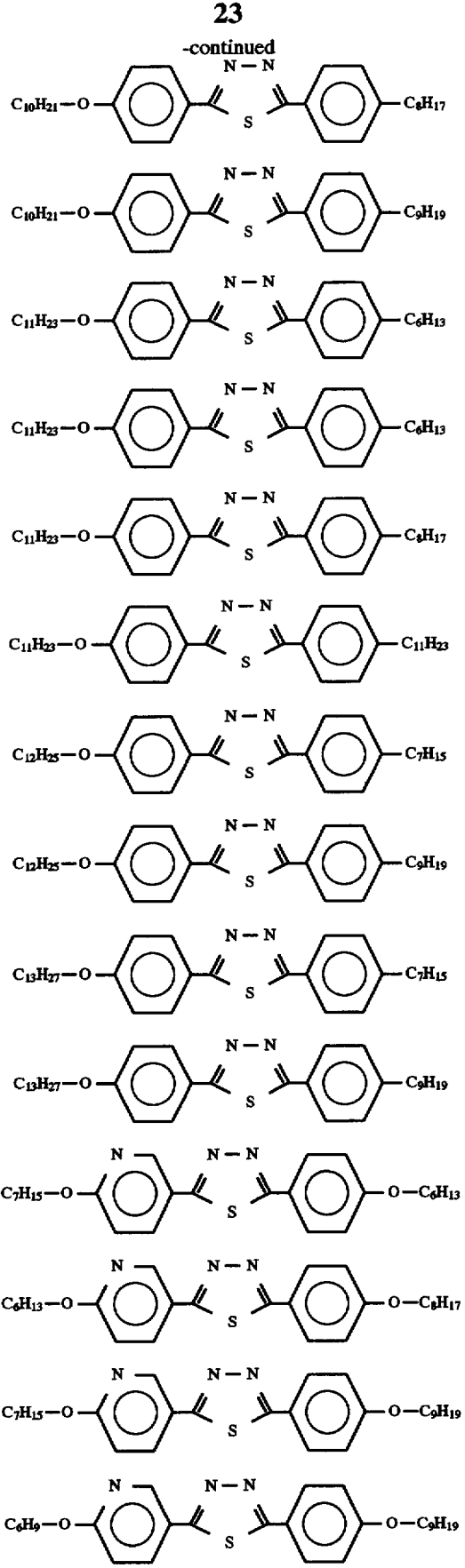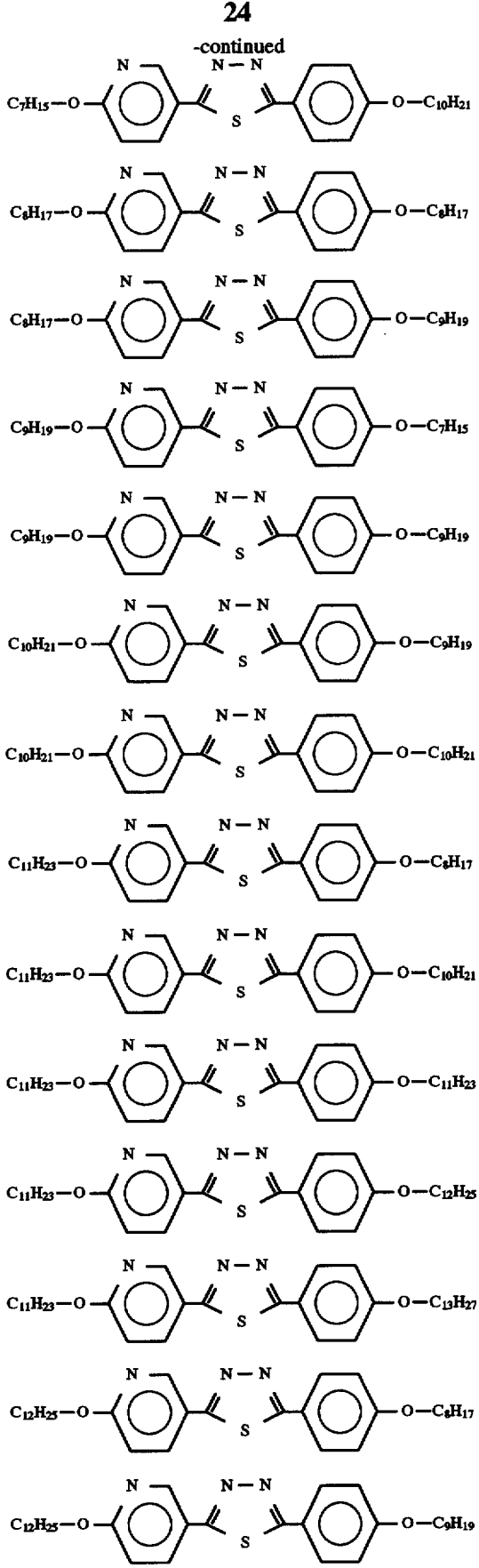

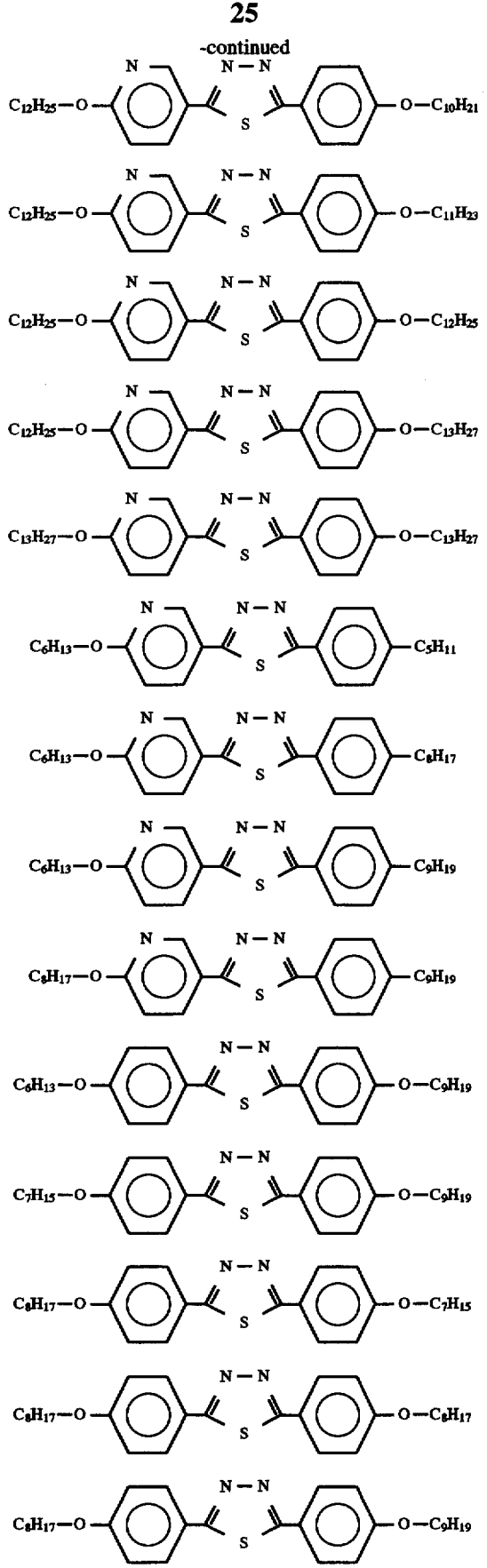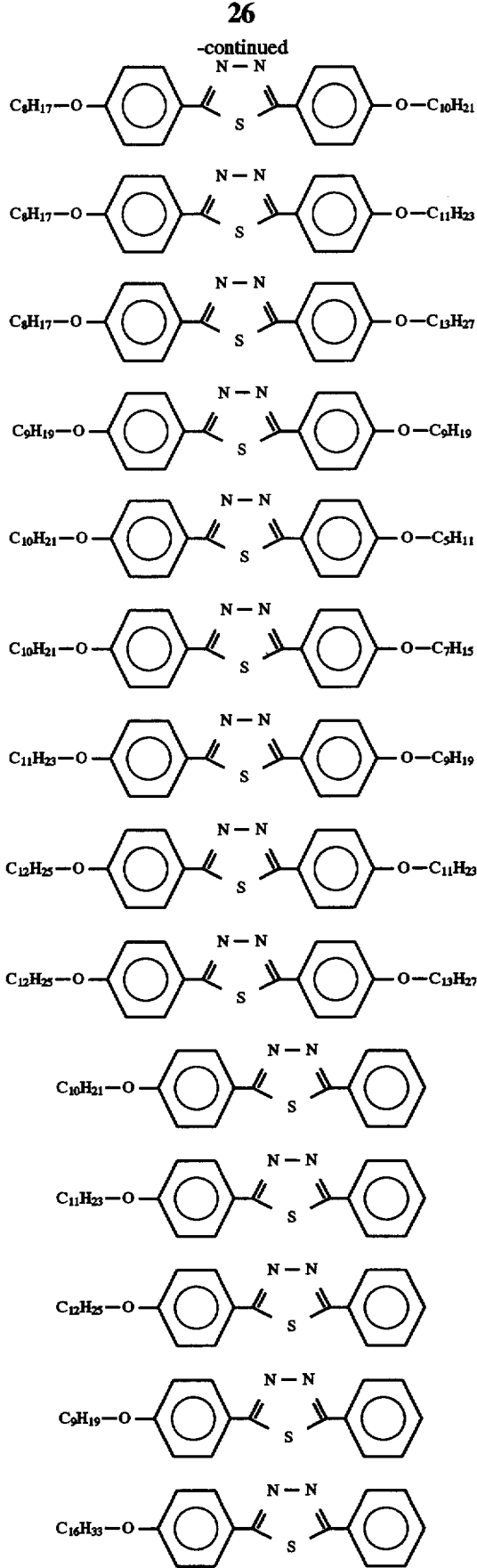

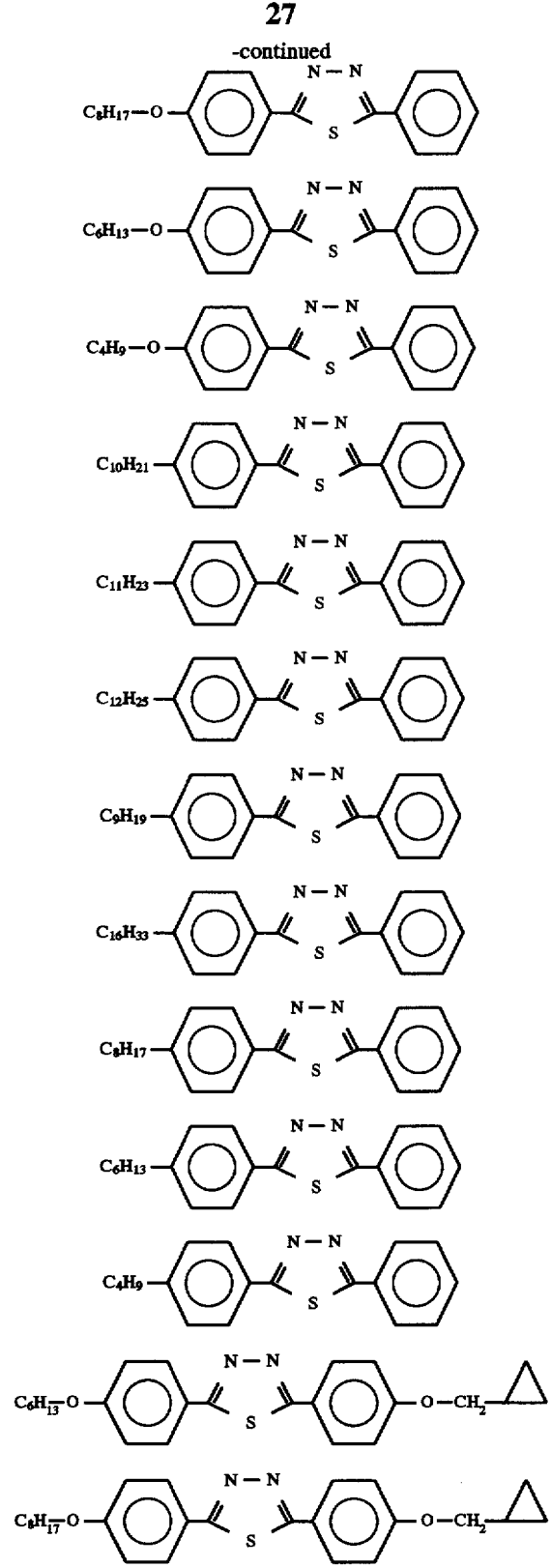
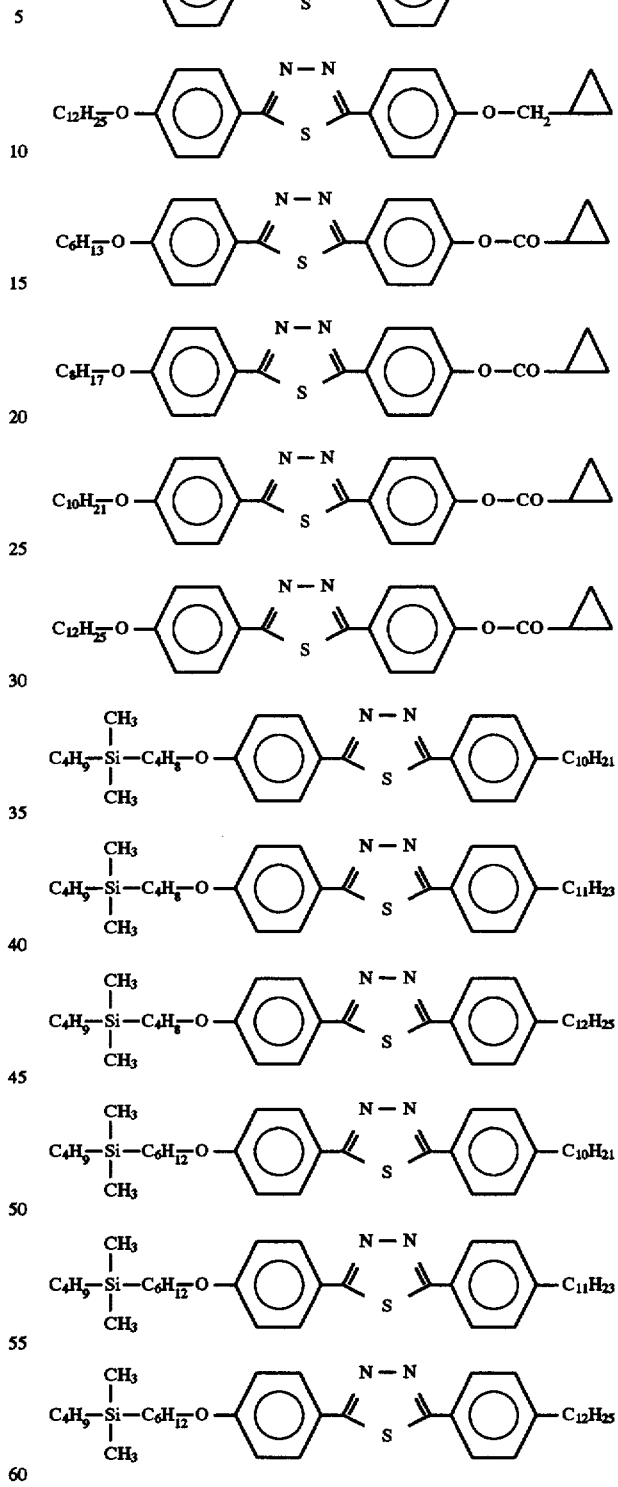

Of the compounds represented by the general formula 3, preferred compounds include the compounds represented by the following general formulae (3a) and (3b):

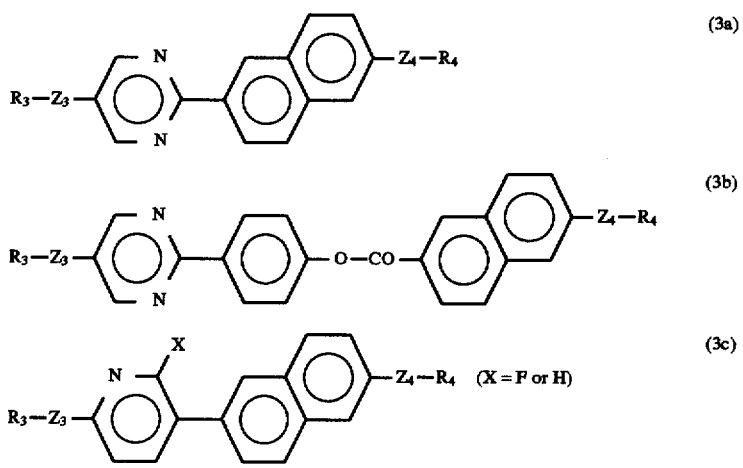

(X=F or H)
wherein $R_3$ and $R_4$ are preferably a group selected from the groups represented by the following formulae (3-i) and (3-ii):

(3-i) an n-alkyl group having from 1 to 16 carbon atoms;
(3-ii)

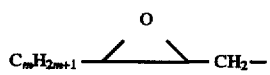

wherein m is an integer of from 1 to 16.

Further, in the compounds represented by the formulae 3, $Z_3$ and $Z_4$ are preferably —O—.

Particularly preferred compounds represented by the general formula 3 include the following compounds.

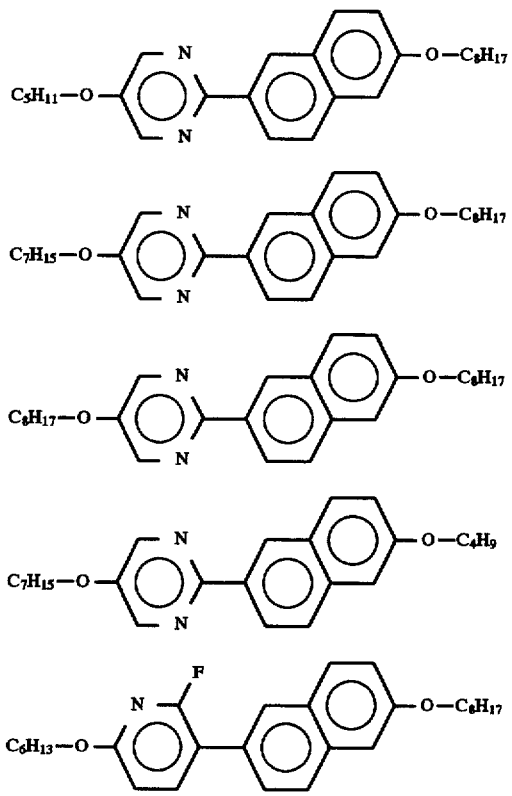

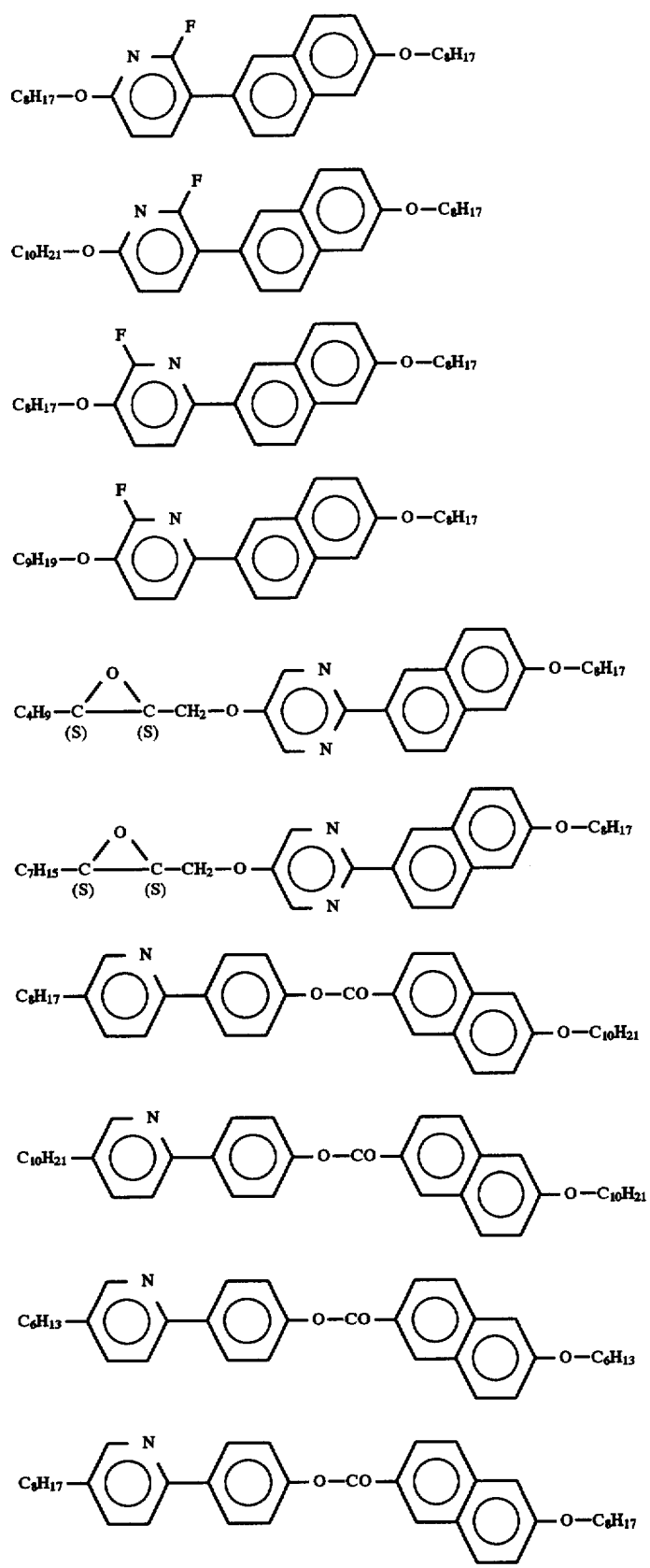

-continued

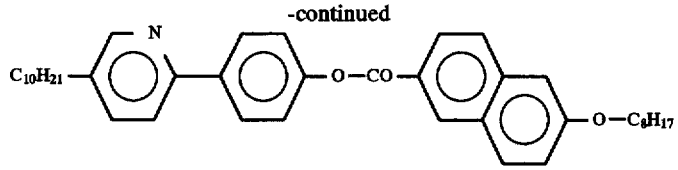

The ferroelectric liquid crystal mixture of the present invention comprises at least one of the compounds of the general formulae 1, 2 or 3. Preferably it comprises at least one compound of the formula 1. More preferably it comprises at least one compound of each of the formulae 1 and 2 or 1 and 3 or 2 and 3. In particular it comprises at least one compound of each of the formulae 1, 2 and 3. By using these compounds in combination, a smaller cone angle can be obtained, and the miscibility in the liquid crystal mixture can be improved so that the melting point of the FLC mixture can be lowered.

The content of each of the compounds of the general formulae 1 to 3 in the liquid crystal mixture is preferably from 5% to 50%, more preferably from 10% to 50% (all percentages are by weight). Also, the mixture according to the present invention may contain phenylpyridine at a concentration of from 10% to 50% together with the compounds of the general formulae 1 to 3.

The present invention is further illustrated in more detail by the following examples.

The general procedure for determining the effective angle and the one angle is as follows:

The mixture is filled into a test cell having a thickness of 2 μm and subjected to field treatment by applying a rectangular pulse of 30 V at 10 Hz for 30 seconds.

To determine the effective angle and the cone angle the measuring cell is mounted on the revolving stage of a polarizing microscope between crossed analyser and polarizer.

By rotating the stage, the position of the stage with minimum light transmission is determined for the two switching states in the cell. The difference between the two positions on the revolving stage is equal to the effective angle if the switching field is turned off and is equal to the cone angle if the switching field is applied during the measurement.

In all examples the determination of the cone angle is made at a temperature 40° C. below the $S_c$-$S_a$ phase transition temperature of the mixture.

EXAMPLE 1

The following compounds were mixed at the indicated weight ratio (%) to prepare a liquid crystal mixture A.

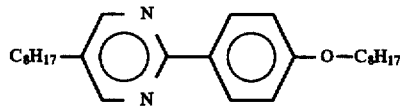

12

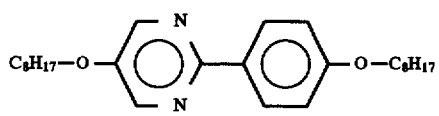

4

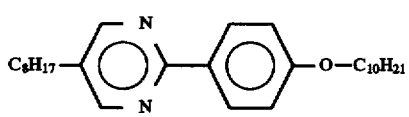

10

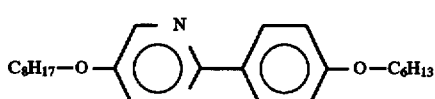

8

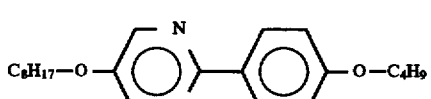

8

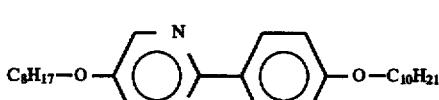

7

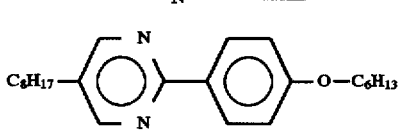

12

[Structures 1, 8, 5, 10, 9, 6 — continued]

Then, the following compounds were mixed with the above-prepared liquid crystal mixture A at the indicated weight ratio (%) to prepare a liquid crystal mixture B.

[Structures with weight ratios: 3, 3, 3, 3, 3, 3]

The resulting liquid crystal mixture B was filled into a cell having a cell thickness of 2 μm, and a rectangular pulse of 30V at 10 Hz was applied for 30 seconds. The quasi-bookshelf texture having a cone angle of 47 degree and an effective angle of 44 degree was observed.

The phase transition temperatures of the liquid crystal mixture B were as follows:

Sc 70.5 Sa 89.5N 96 I

Comparative Example 1

In the same manner as described in Example 1, the liquid crystal mixture A was filled into the cell having a cell thickness of 2 μm, and a rectangular pulse of 30V at 10 Hz was applied for 30 seconds. As a result, the quasi-bookshelf texture having a cone angle of 50 degree and an effective angle of 48 was observed.

The phase transition temperatures of the liquid crystal mixture A were as follows:

Sc 69 Sa 86.5N 93 I

The liquid crystal mixture A comprises typical phenylpyrimidines, and, as compared with the liquid crystal mixture B, the cone angle is higher than that of the mixture B by 3 degree, while the Sc/Sa phase transition temperature is lower than that of the mixture B by 1.5 degree. Also, the effective angle is as high as 45 degree, and the transmission shown by the liquid crystal mixture is slightly low. This indicates that the compounds according to the present invention are very useful for improving the transmission and speed by reducing the cone angle of the conventional phenylpyrimidine liquid crystal mixtures.

EXAMPLE 2

The following compounds were mixed at the indicated weight ratio (%) to prepare a liquid crystal mixture C.

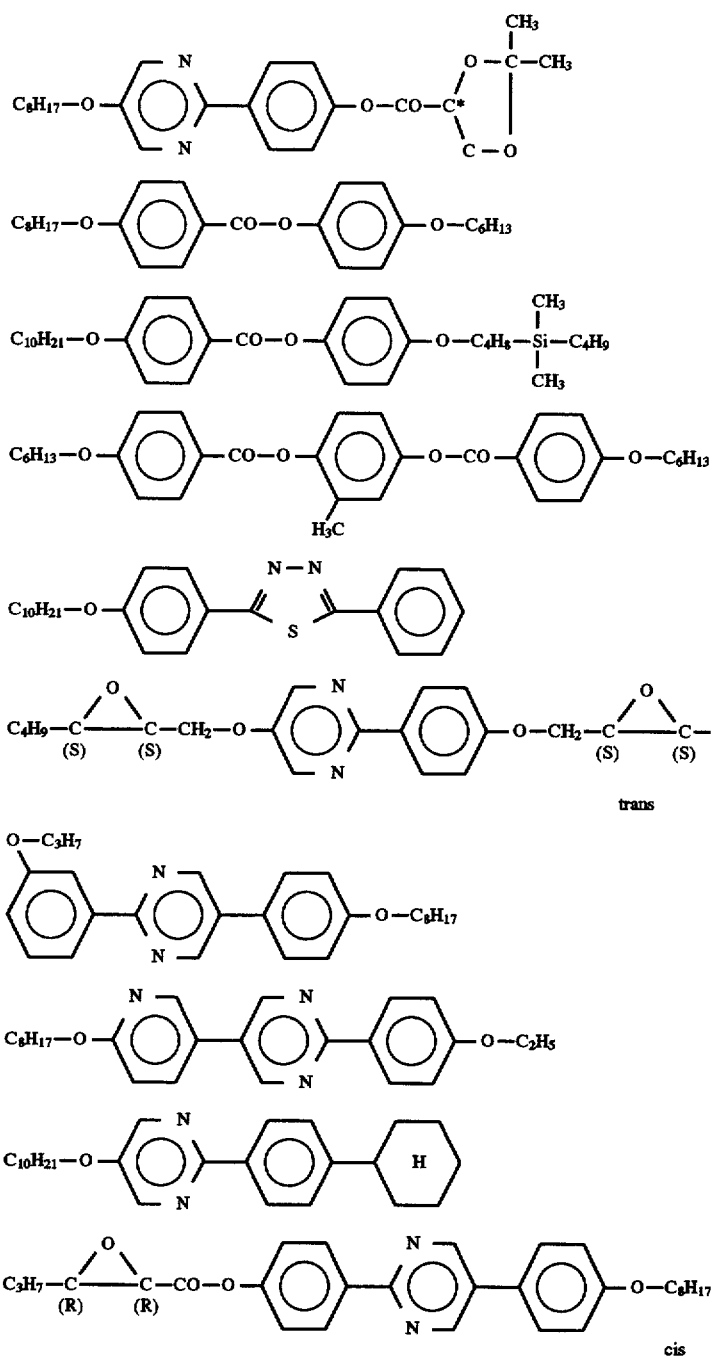
Then, the following compounds were mixed with the above-prepared liquid crystal mixture C at the indicated weight ratio (%) to prepare a liquid crystal mixture D.
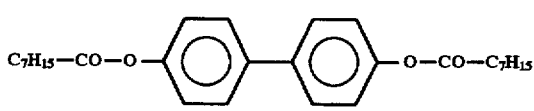

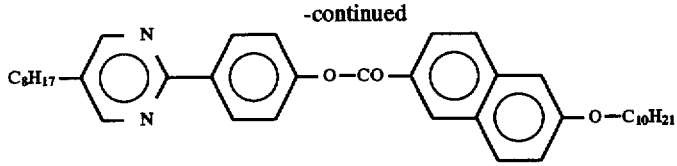

7

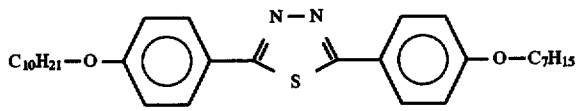

6

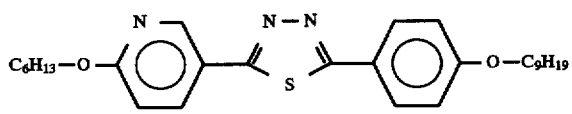

3

The resulting liquid crystal mixture D was filled into a cell having a cell thickness of 2 μm, and a rectangular pulse of 30V at 10 Hz was applied for 30 seconds. The quasi-bookshelf texture having e cone angle of 32 degree and an effective angle of 29 degree was observed. The switching speed was 90 μs.

The phase transition temperatures of the liquid crystal mixture D were as follows:

Sc 60 Sa 90N 108 I

Comparative Example 2

In the same manner as described in Example 2, the following compound was mixed in an amount of 20% by weight with the liquid crystal mixture C to prepare a liquid crystal mixture E having similar phase transition temperatures to 15 those of the liquid crystal mixture D.

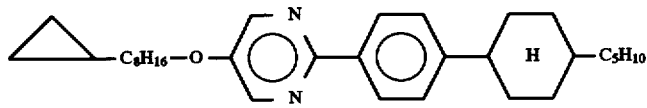

In the same manner as described in Example 1, the resulting liquid crystal mixture E was filled into a cell having a cell thickness of 2 μm, and a rectangular pulse of 30V at 10 Hz was applied for 30 seconds. The quasi-bookshelf texture having a cone angle of 40 degree and an effective angle of 37 degree was observed. The switching speed was 110 μs.

The phase transition temperatures of the liquid crystal mixture E were as follows:

Sc 50 Sa 86.5N 93 I

The liquid crystal mixture E comprises typical phenylpyrimidine and phenylbenzoic acid ester compounds, and, as compared with the liquid crystal.

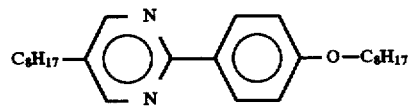

12

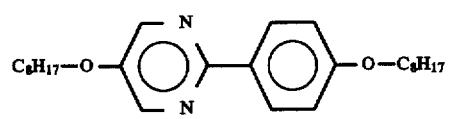

4

-continued

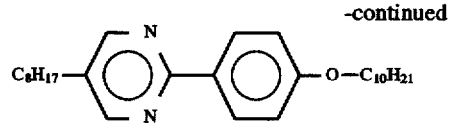 10

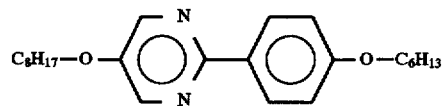 9

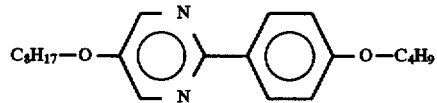 8

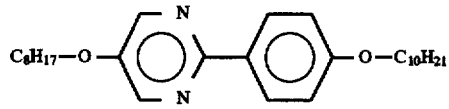 8

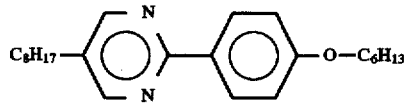 12

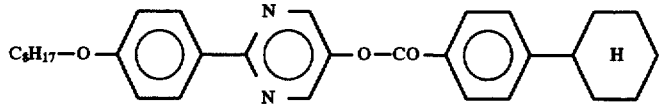 5

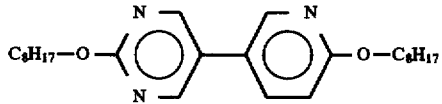 5

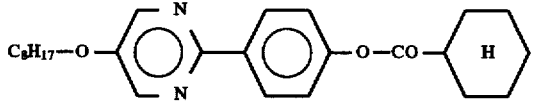 9

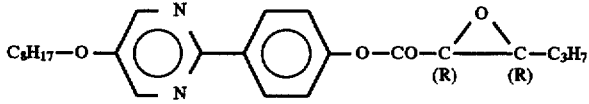 6

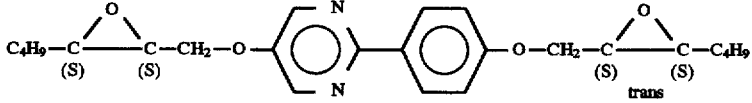 6

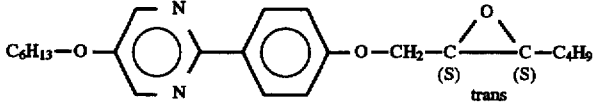 6

The resulting liquid crystal mixture F was filled into a cell having a cell thickness of 2 μm, and a rectangular pulse of 30V at 10 Hz was applied for 30 seconds. The quasi-bookshelf texture having a cone angle of 48 degree and an effective angle of 44 degree was observed.

The phase transition temperatures of the liquid crystal mixture B were as follows:

X −8 Sc 63 Sa 79N 84 I

The compound of the following formula (g), (h) or (i) was mixed with the resulting liquid crystal mixture F in an amount of 8% by weight to prepare liquid crystal mixtures G, H and I.

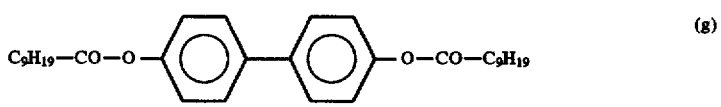 (g)

-continued

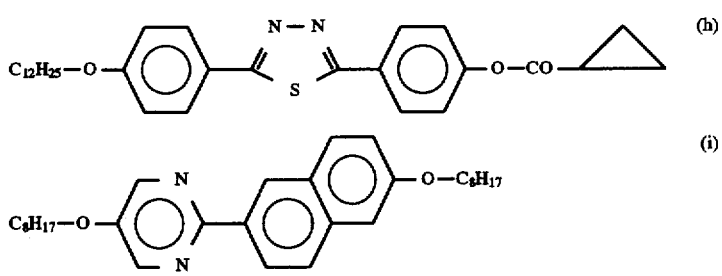

The phase transition temperatures end the cone angle of each of the liquid crystal compositions G, H and I were as follows:

Liquid Crystal Cone
Example Mixture Phase Transition Temperature Angle
3 G Sc 63 Sa 78N 81 I 46
4 H Sc 67 Sa 80N 86 I 46
5 I Sc 64 Sa 80N 86 I 46

EXAMPLE 6

The compounds shown below were mixed with the liquid crystal mixture F obtained in Example 3 at the weight ratio (%) shown below to prepare a liquid crystal mixture J.

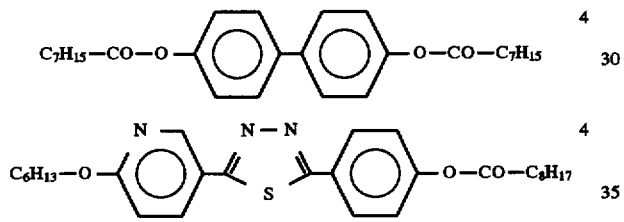

The cone angle, the effective angle and the phase transition temperatures of the resulting liquid crystal mixture J were as follows:

Cone Angle: 47 degree
Effective Angle: 45 degree
Phase Transition Temperatures: Sc 65 Sa 82N 84 I The liquid crystal mixture J containing the specific compounds according to the present invention exhibited an excellent property of reduced cone angle, in spite of the increased phase transition temperatures as compared with the liquid crystal mixture F.

EXAMPLE 7

The compounds shown below were mixed with the liquid crystal mixture F obtained in Example 3 at the weight ratio (%) shown below to prepare a liquid crystal mixture K.

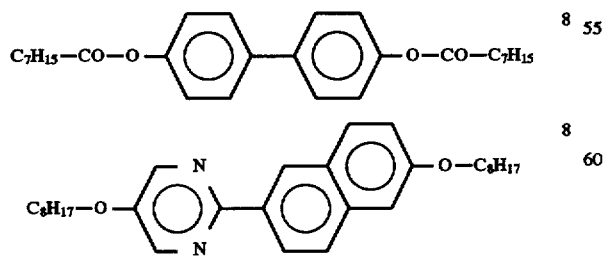

The cone angle, the effective angle and the phase transition temperatures of the resulting liquid crystal mixture K were as follows:

Cone Angle: 45 degree
Effective Angle: 43 degree
Phase Transition Temperatures: Sc 63 Sa 79N 84 I The liquid crystal mixture K containing the specific compounds according to the present invention exhibited an excellent property of reduced cone angle, in spite of the increased phase transition temperatures as compared with the liquid crystal mixture F.

What is claimed is:

1. A ferroelectric liquid crystal mixture comprising at least one of the compounds of each of the formulae 1 and 2 or formulae 1 and 3 or at least one compound of each of the general formulae 1 to 3, and having a Sc/Sa phase transition temperature of 60° C. or more and a cone angle of 47 degrees or less at a temperature between 15° C. and 35° C.:

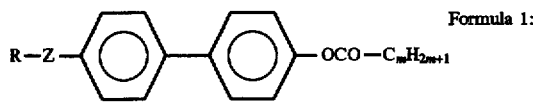

wherein
m is an integer of from 1 to 16;
R represents
(a) a straight chain alkyl group having from 2 to 16 carbon atoms, in which one or two non-adjacent —$CH_2$— groups may be substituted with —O—, —CO—O—, —O—CO—, —Si$(CH_3)_2$—; and a terminal methyl group may be substituted with a cyclopropyl group; or
(b):

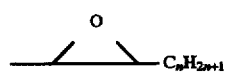

wherein n is an integer of from 1 to 10; and
Z is a single bond, —O—, —CO—O—, —O—CO—, —O—$CH_2$— or —$CH_2$—O—; provided that, when R is (b), Z is —CO—O— or —$CH_2$—O—;

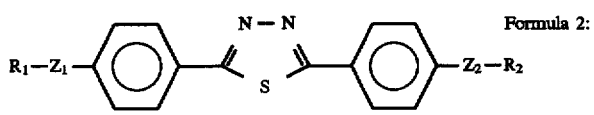

wherein at least one optional =C—H group of the aromatic ring may be substituted with =N—;
$R_1$ and $R_2$ each independently represents
(a) a hydrogen atom;
(b) a straight chain or branched chain alkyl group having from 2 to 16 carbon atoms, in which one or two non-adjacent —$CH_2$— groups may be substituted with —O—, —CO—O—, —O—CO—, —Si(CH₃)₂—; and a terminal methyl group may be substituted with a cyclopropyl group; or
(c):

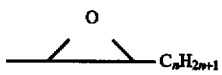

wherein n is an integer of from 1 to 10; and
Z₁ and Z₂ each represents a single bond, —O—, —CO—O—, —O—CO—, —O—CH₂— or —CH₂—O—; provided that, when R₁ is (c), Z₁ is —CO—O— or —CH₂—O—, and that, when R₂ is (c), Z₂ is —O—CO— or —OCH₂—; and

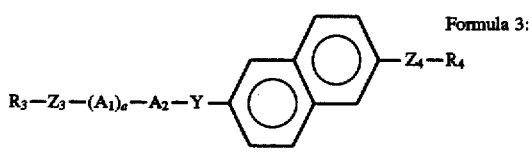

(c):

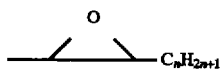

wherein n is an integer of from 1 to 10; and
Z₁ and Z₂ each represents a single bond, —O—, —CO—O—, —O—CO—, —O—CH₂— or —CH₂—O—; provided that, when R₁ is (c), Z₁ is —CO—O— or —CH₂—O—, and that, when R₂ is (c), Z₂ is —O—CO— or —O—CH₂—; and

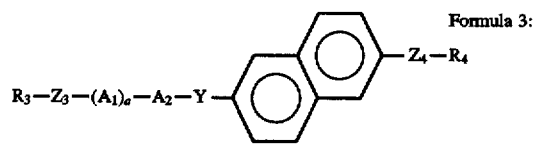

wherein A₁ and A₂, which may be the same or different, each represents 1,4-phenylene, pyridine-2,5-diyl or pyrimidine-2,5-diyl in which one or two hydrogen atoms may be substituted with F;
a is 0 or 1;
R₃ and R₄ each independently represents
(a) a hydrogen atom;
(b) a straight chain or branched chain alkyl group having from 2 to 16 carbon atoms, in which one or two non-adjacent —CH₂— groups may be substituted with —O—, —CO—O—, —O—CO—, —Si(CH₃)₂—, a chiral epoxy group or —O—CO—O—, and a terminal methyl group may be substituted with a cyclopropyl group; or
(c):

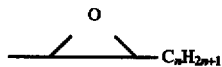

wherein n is an integer of from 1 to 10;
Y is a single bond, —O—CO—, —CO—O—, —O—CH₂— or —CH₂—O—; and Z₃ and Z₄ each represents a single bond, —O—, —CO—O—, —O—CO—, —CH₂—O— or —O—CH₂—; provided that, when R₃ is (c), Z₃ is —CO—O— or —CH₂—O—, and that, when R₄ is (c), Z₄ is —O—CO— or —O—CH₂—.

2. A ferroelectric liquid crystal mixture as claimed in claim 1, comprising each compound or group of compounds of the general formulae 1, 2 and 3 in a concentration of from 10% to 50% by weight.

3. A ferroelectric liquid crystal mixture comprising at least one compound from at least two of formulae 1, 2 and 3, and having a Sc/Sa phase transition temperature of 60° C. or more and a cone angle of 47 degree or less at a temperature between 15° C. and 35° C.:

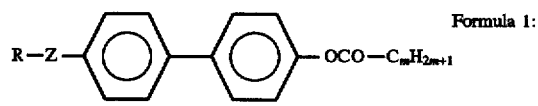

wherein m is an integer of from 1 to 16; and R represents a straight chain alkyl group having from 2 to 16 carbon atoms, in which one or two non-adjacent —CH₂— groups may be substituted with —O—, —CO—O— or —O—CO—, and a terminal methyl group may be substituted with a cyclopropyl group; and Z is a single bond, —O—, —CO—O— or —O—CO—;

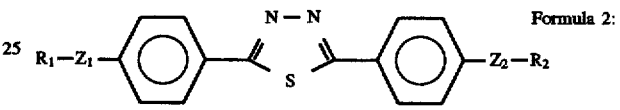

wherein at least one optional =C—H group of the aromatic ring may be substituted with [=C—F] or =N—;
R₁ and R₂ each independently represents
(a) a hydrogen atom;
(b) a straight chain or branched chain alkyl group having from 2 to 16 carbon atoms, in which one or two non-adjacent —CH₂— groups may be substituted with —O—, —CO—O—, —O—CO—, —Si(CH₃)₂—, and a terminal methyl group may be substituted with a cyclopropyl group; or
(c):

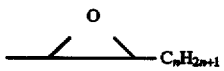

wherein n is an integer of from 1 to 10; and
Z₁ and Z₂ each represents a single bond, —O—, —CO—O—, —O—CO—, —O—CH₂— or —CH₂—O—; provided that, when R₁ is (c), Z₁ is —CO—O— or —CH₂—O—, and that, when R₂ is (c), Z₂ is —O—CO— or —O—CH₂—; and

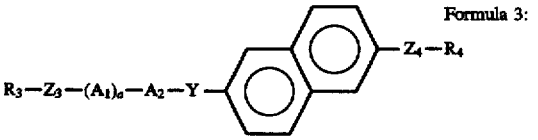

wherein A₁ and A₂, which may be the same or different, each represents 1,4-phenylene, pyridine-2,5-diyl or pyrimidine-2,5-diyl in which one or two hydrogen atoms may be substituted with F;
a is 0 or 1;
R₃ and R₄ each independently represents
(a) a hydrogen atom;
(b) a straight chain or branched chain alkyl group having from 2 to 16 carbon atoms, in which one or two non-adjacent —CH₂— groups may be substituted with —O—, —CO—O—, —O—CO—, —Si(CH₃)₂—, a chiral epoxy group or —O—CO—O—, and a terminal methyl group may be substituted with a cyclopropyl group; or (c):

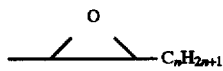

wherein n is an integer of from 1 to 10;

Y is a single bond, —O—CO—, —CO—O—, —O—CH₂— or —CH₂—O—; and Z₃ and Z₄ each represents a single bond, —O—, —CO—O—, —O—CO—, —CH₂—O— or —O—CH₂—; provided that, when R₃ is (c), Z₃ is —CO—O— or —CH₂—O—, and that, when R₄ is (c), Z₄ is —O—CO— or —O—CH₂—.

4. A ferroelectric liquid crystal mixture comprising at least one of the compounds of each of the formulae 1 and 2 or formulae 1 and 3 or at least one compound of each of the general formulae 1 to 3, and having a Sc/Sa phase transition temperature of 60° C. or more and a cone angle of 47 degrees or less:

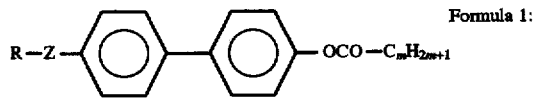

Formula 1:

wherein m is an integer of from 1 to 16;

R represents:
(a) a straight chain alkyl group having from 2 to 16 carbon atoms, in which one or two non-adjacent —CH₂— groups may be substituted with —O—, —CO—O—, —O—CO—, —Si(CH₃)₂—; and a terminal methyl group may be substituted with a cyclopropyl group; or (b):

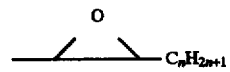

wherein n is an integer of from 1 to 10; and

Z is a single bond, —O—, —CO—O—, —O—CO—, —O—CH₂— or —CH₂—O—; provided that, when R is (b), Z is —CO—O— or —CH₂—O—;

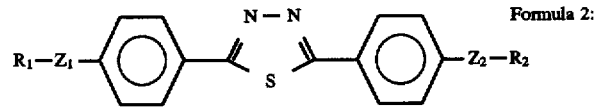

Formula 2:

wherein at least one optional =C—H group of the aromatic ring may be substituted with =N—;

R₁ and R₂ each independently represents:
(a) a hydrogen atom;
(b) a straight chain or branched chain alkyl group having from 2 to 16 carbon atoms, in which one or two non-adjacent —CH₂— groups may be substituted with —O—, —CO—O—, —O—CO—, —Si(CH₃)₂—; and a terminal methyl group may be substituted with a cyclopropyl group; or (c):

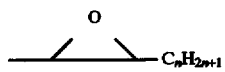

wherein n is an integer of from 1 to 10; and

Z₁ and Z₂ each represents a single bond, —O—, —CO—O—, —O—CO—, —O—CH₂— or —CH₂—O—; provided that, when R₁ is (c), Z₁ is —CO—O— or —CH₂—O—, and that, when R₂ is (c), Z₂ is —O—CO— or —O—CH₂—; and

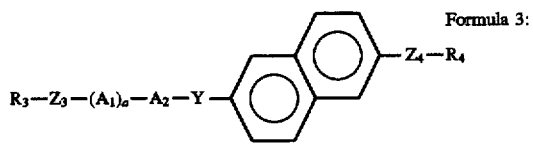

Formula 3:

wherein A₁ and A₂, which may be the same or different, each represents 1,4-phenylene in which one or two hydrogen atoms may be substituted with F or pyridine-2,5-diyl or pyrimidine-2,5-diyl in which one or two hydrogen atoms may be substituted with F;

a is 0 or 1; and

R₃ and R₄ each independently represents:
(a) a hydrogen atom;
(b) a straight chain or branched chain alkyl group having from 2 to 16 carbon atoms, in which one or two non-adjacent —CH₂— groups may be substituted with —O—, —CO—O—, —O—CO, —Si(CH₃)₂—; and a terminal methyl group may be substituted with a cyclopropyl group; or (c):

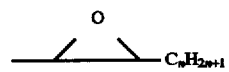

wherein n is an integer of from 1 to 10;

Y is a single bond, —O—CO—, —CO—O—, —O—CH₂— or —CH₂—O—; and

Z₃ and Z₄ each represents a single bond, —O—, —CO—O—, —O—CO—, —CH₂—O— or —O—CH₂—; provided that, when R₃ is (c), Z₃ is —CO—O— or —CH₂—O—, and that, when R₄ is (c), Z₄ is —O—CO— or —O—CH₂—.

5. A ferroelectric liquid crystal mixture comprising at least one of the compounds of each of the formulae 1 and 2 or formulae 1 and 3 or at least one compound of each of the general formulae 1 to 3, and having a Sc/Sa phase transition temperature of 60° C. or more and a cone angle of 47 degrees or less:

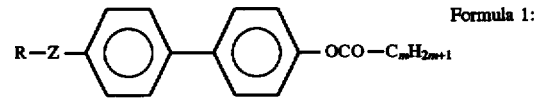

Formula 1:

wherein m is an integer of from 1 to 16; and

R represents a straight chain alkyl group having from 2 to 16 carbon atoms, in which one or two non-adjacent —CH₂— groups may be substituted with —O—, —CO—O— or —O—CO—, and a terminal methyl group may be substituted with a cyclopropyl group; and Z is a single bond, —O—, —CO—O— or —O—CO—;

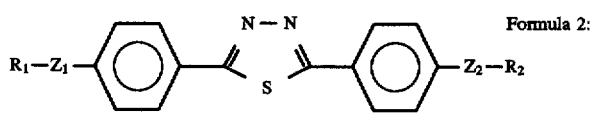

Formula 2:

wherein at least one optional =C—H group of the aromatic ring may be substituted with =N—;

$R_1$ and $R_2$ each independently represents:
(a) a hydrogen atom;
(b) a straight chain or branched chain alkyl group having from 2 to 16 carbon atoms, in which one or two non-adjacent —$CH_2$— groups may be substituted with —O—, —CO—O—, —O—CO—, —Si($CH_3$)$_2$—, and a terminal methyl group may be substituted with a cyclopropyl group; or
(c):

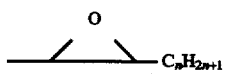

wherein n is an integer of from 1 to 10; and $Z_1$ and $Z_2$ each represents a single bond, —O—, —CO—O—, —O—CO—, —O—$CH_2$— or —$CH_2$—O—; provided that, when $R_1$ is (c), $Z_1$ is —CO—O— or —$CH_2$—O—, and that, when $R_2$ is (c), $Z_2$ is —O—CO— or —O—$CH_2$—; and

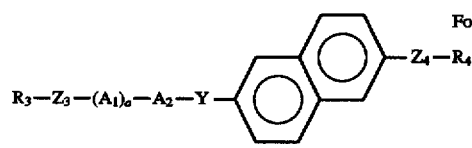

Formula 3:

wherein $A_1$ and $A_2$, which may be the same or different, each represents 1,4-phenylene, pyridine-2,5-diyl or pyrimidine-2,5-diyl in which one or two hydrogen atoms may be substituted with F;

a is 0 or 1;

$R_3$ and $R_4$ each independently represents:
(a) a hydrogen atom;
(b) a straight chain or branched chain alkyl group having from 2 to 16 carbon atoms, in which one or two non-adjacent —$CH_2$— groups may be substituted with —O—, —CO—O—, —O—CO—, —Si($CH_3$)$_2$—, a chiral epoxy group or —O—CO—O—, and a terminal methyl group may be substituted with a cyclopropyl group; or
(c):

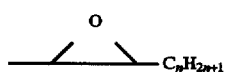

wherein n is an integer of from 1 to 10; Y is a single bond, —O—CO—, —CO—O—, —O—$CH_2$— or —$CH_2$—O—; and $Z_3$ and $Z_4$ each represents a single bond, —O—, —CO—O—, —O—CO—, —$CH_2$—O— or —O—$CH_2$—; provided that, when $R_3$ is (c), $Z_3$ is —CO—O— or —$CH_2$—O—, and that, when $R_4$ is (c), $Z_4$ is —O—CO— or —O—$CH_2$—.

6. A ferroelectric liquid crystal mixture comprising at least one of the compounds of each of the formulae 1 and 2 or formulae 1 and 3 or at least one compound of each of the general formulae 1 to 3, and having a Sc/Sa phase transition temperature of 60° C. or more and a cone angle of 47 degrees or less:

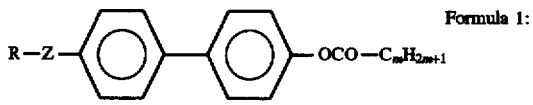

Formula 1:

wherein m is an integer of from 1 to 16;

R represents:
(a) a straight chain alkyl group having from 2 to 16 carbon atoms, in which one or two non-adjacent —$CH_2$— groups may be substituted with —O—, —CO—O—, —O—CO—, —Si($CH_3$)$_2$—; and a terminal methyl group may be substituted with a cyclopropyl group; or
(b):

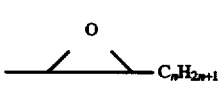

wherein n is an integer of from 1 to 10; and

Z is a single bond, —O—, —CO—O—, —O—CO—, —O—$CH_2$— or —$CH_2$—O—; provided that, when R is (b), Z is —CO—O— or —$CH_2$—O—;

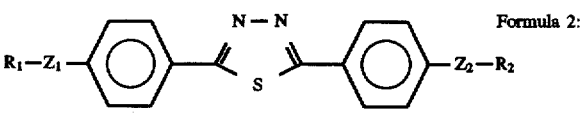

Formula 2:

wherein at least one optional =C—H group of the aromatic ring may be substituted with =N—;

$R_1$ and $R_2$ each independently represents:
(a) a hydrogen atom;
(b) a straight chain or branched chain alkyl group having from 2 to 16 carbon atoms, in which one or two non-adjacent —$CH_2$— groups may be substituted with —O—, —CO—O—, —O—CO—, —Si($CH_3$)$_2$—; and a terminal methyl group may be substituted with a cyclopropyl group; or
(c):

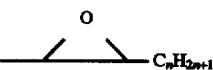

wherein n is an integer of from 1 to 10; and $Z_1$ and $Z_2$ each represents a single bond, —O—, —CO—O—, —O—CO—, —O—$CH_2$— or —$CH_2$—O—; provided that, when $R_1$ is (c), $Z_1$ is —CO—O— or —$CH_2$—O—, and that, when $R_2$ is (c), $Z_2$ is —O—CO— or —O—$CH_2$—; and

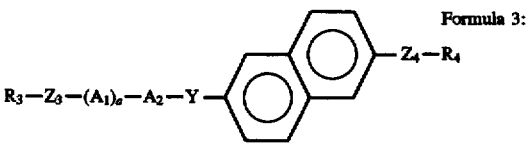

Formula 3:

wherein $A_1$ and $A_2$, which may be the same or different, each represents 1,4-phenylene in which one or two hydrogen atoms may be substituted with F or pyridine-2,5-diyl or pyrimidine-2,5-diyl in which one or two hydrogen atoms may be substituted with F;

a is 0 or 1; and

R$_3$ and R$_4$ each independently represents:
(a) a hydrogen atom;
(b) a straight chain or branched chain alkyl group having from 2 to 16 carbon atoms, in which one or two non-adjacent —CH$_2$— groups may be substituted with —O—, —CO—O—, —O—CO— or —Si(CH$_3$)$_2$—; and a terminal methyl group may be substituted with a cyclopropyl group; or
(c):

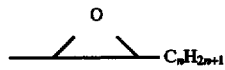

wherein n is an integer of from 1 to 10; Y is a single bond or —O—CO—; and Z$_3$ and Z$_4$ each represents a single bond, —O—, —CO—O—, —O—CO—, —CH$_2$—O— or —O—CH$_2$—; provided that, when R$_3$ is (c), Z$_3$ is —CO—O— or —CH$_2$—O—, and that, when R$_4$ is (c), Z$_4$ is —O—CO— or —O—CH$_2$—.

7. A ferroelectric liquid crystal mixture comprising at least one of the compounds of each of the formulae 1 and 2 or formulae 1 and 3 or at least one compound of each of the general formulae 1 to 3, and having a Sc/Sa phase transition temperature of 60° C. or more and a cone angle of 47 degrees or less:

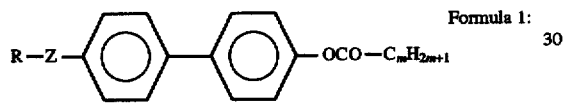

Formula 1:

wherein m is an integer of from 1 to 16; and R represents a straight chain alkyl group having from 2 to 16 carbon atoms, in which one or two non-adjacent —CH$_2$— groups may be substituted with —O—, —CO—O— or —O—CO—, and a terminal methyl group may be substituted with a cyclopropyl group; and Z is a single bond, —O—, —CO—O— or —O—CO—;

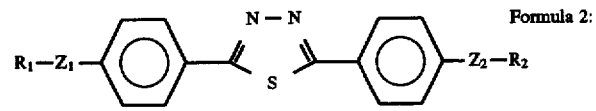

Formula 2:

wherein at least one optional =C—H group of the aromatic ring may be substituted with =N—;

R$_1$ and R$_2$ each independently represents:
(a) a hydrogen atom;
(b) a straight chain or branched chain alkyl group having from 2 to 16 carbon atoms, in which one or two non-adjacent —CH$_2$— groups may be substituted with —O—, —CO—O—, —O—CO—, —Si(CH$_3$)$_2$—, and a terminal methyl group may be substituted with a cyclopropyl group; or
(c):

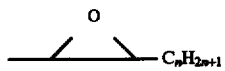

wherein n is an integer of from 1 to 10; and

Z$_1$ and Z$_2$ each represents a single bond, —O—, —CO—O—, —O—CO—, —O—CH$_2$— or —CH$_2$—O—; provided that, when R$_1$ is (c), Z$_1$ is —CO—O— or —CH$_2$—O—, and that, when R$_2$ is (c), Z$_2$ is —O—CO— or —O—CH$_2$—; and

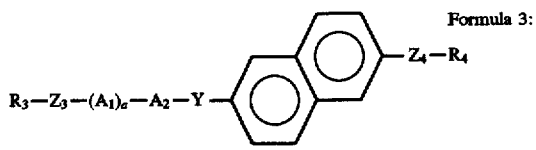

Formula 3:

wherein A$_1$ and A$_2$, which may be the same or different, each represents 1,4-phenylene, pyridine-2,5-diyl or pyrimidine-2,5-diyl in which one or two hydrogen atoms may be substituted with F;

a is 0 or 1;

R$_3$ and R$_4$ each independently represents:
(a) a hydrogen atom;
(b) a straight chain or branched chain alkyl group having from 2 to 16 carbon atoms, in which one or two non-adjacent —CH$_2$— groups may be substituted with —O—, —CO—O—, —O—CO—, —Si(CH$_3$)$_2$—, and a terminal methyl group may be substituted with a cyclopropyl group; or
(c):

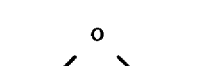

wherein n is an integer of from 1 to 10; Y is a single bond or —O—CO—; and

Z$_3$ and Z$_4$ each represents a single bond, —O—, —CO—O—, —O—CO—, —CH$_2$—O— or —O—CH$_2$—; provided that, when R$_3$ is (c), Z$_3$ is —CO—O— or —CH$_2$—O—, and that, when R$_4$ is (c), Z$_4$ is —O—CO— or —O—CH$_2$—.

* * * * *